United States Patent
Kiryukhin et al.

(10) Patent No.: US 10,241,099 B2
(45) Date of Patent: Mar. 26, 2019

(54) FILM SENSOR

(71) Applicants: Agency for Science, Technology and Research, Singapore (SG); Massey University, Palmerston North (NZ)

(72) Inventors: Maxim Kiryukhin, Singapore (SG); Anton Sadovoy, Singapore (SG); Vladimir Korzh, Singapore (SG); Cathleen Teh, Singapore (SG); Harjinder Singh, Palmerston North (NZ); Mita Lad, Palmerston North (NZ)

(73) Assignees: Agency for Science, Technology and Research, Singapore (SG); Massey University (NZ)

( * ) Notice: Subject to any disclaimer, the term of this patent is extended or adjusted under 35 U.S.C. 154(b) by 0 days.

(21) Appl. No.: 15/125,405

(22) PCT Filed: Mar. 19, 2015

(86) PCT No.: PCT/SG2015/050043
§ 371 (c)(1),
(2) Date: Sep. 12, 2016

(87) PCT Pub. No.: WO2015/142289
PCT Pub. Date: Sep. 24, 2015

(65) Prior Publication Data
US 2017/0074850 A1    Mar. 16, 2017

(30) Foreign Application Priority Data

Mar. 20, 2014 (SG) .......................... 10201400820Q

(51) Int. Cl.
*G01N 33/12* (2006.01)
*G01N 21/64* (2006.01)
(Continued)

(52) U.S. Cl.
CPC ......... *G01N 33/12* (2013.01); *G01N 21/6428* (2013.01); *G01N 21/80* (2013.01);
(Continued)

(58) Field of Classification Search
CPC ..... G01N 2021/6439; G01N 2021/775; G01N 2021/7786; G01N 2021/7796;
(Continued)

(56) References Cited

U.S. PATENT DOCUMENTS 4,003,709 A    1/1977 Eaton et al.
4,285,697 A    8/1981 Neary
(Continued)

OTHER PUBLICATIONS

International Search Report for PCT/SG2015/050043, 5 pages (dated Sep. 12, 2016).
(Continued)

*Primary Examiner* — Samuel P Siefke
(74) *Attorney, Agent, or Firm* — Choate, Hall & Stewart LLP

(57) ABSTRACT

The present disclosure relates to a sensor for indicating food quality comprising a semi-permeable film layer, the semi-permeable film layer comprising at least one integrally formed well having at least one sensing element disposed therein; wherein the well is sealed by a second film layer, the semi-permeable film layer being impermeable to said sensing element but is permeable to at least one analyte detectable by said sensing element.

19 Claims, 8 Drawing Sheets

(51) Int. Cl.
  *G01N 21/80* (2006.01)
  *G01N 21/77* (2006.01)
  *G01N 31/22* (2006.01)

(52) U.S. Cl.
  CPC .......... *G01N 31/22* (2013.01); *G01N 31/221* (2013.01); *G01N 31/223* (2013.01); *G01N 31/229* (2013.01); *G01N 2021/6439* (2013.01); *G01N 2021/775* (2013.01); *G01N 2021/7786* (2013.01); *G01N 2021/7796* (2013.01)

(58) Field of Classification Search
  CPC .... G01N 21/6428; G01N 21/80; G01N 31/22; G01N 31/221; G01N 31/223; G01N 31/229; G01N 33/12; A61B 34/25; A61B 34/30; A61G 13/02; A61G 2203/16
  See application file for complete search history.

(56) References Cited

U.S. PATENT DOCUMENTS

| | | |
|---|---|---|
| 5,407,829 A | 4/1995 | Wolfbeis et al. |
| 6,589,779 B1 | 7/2003 | McDevitt et al. |

OTHER PUBLICATIONS

Written Opinion for PCT/SG2015/050043, 5 pages (dated Sep. 12, 2016).

[Fig. 1]
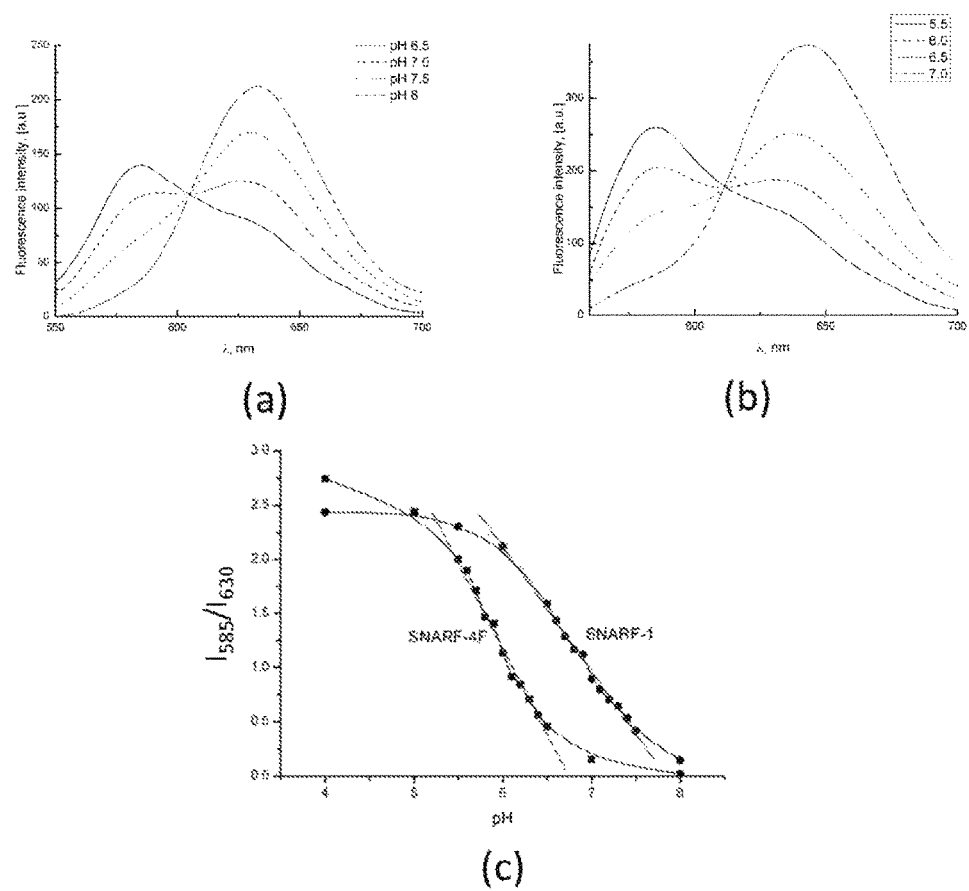

[Fig. 2]
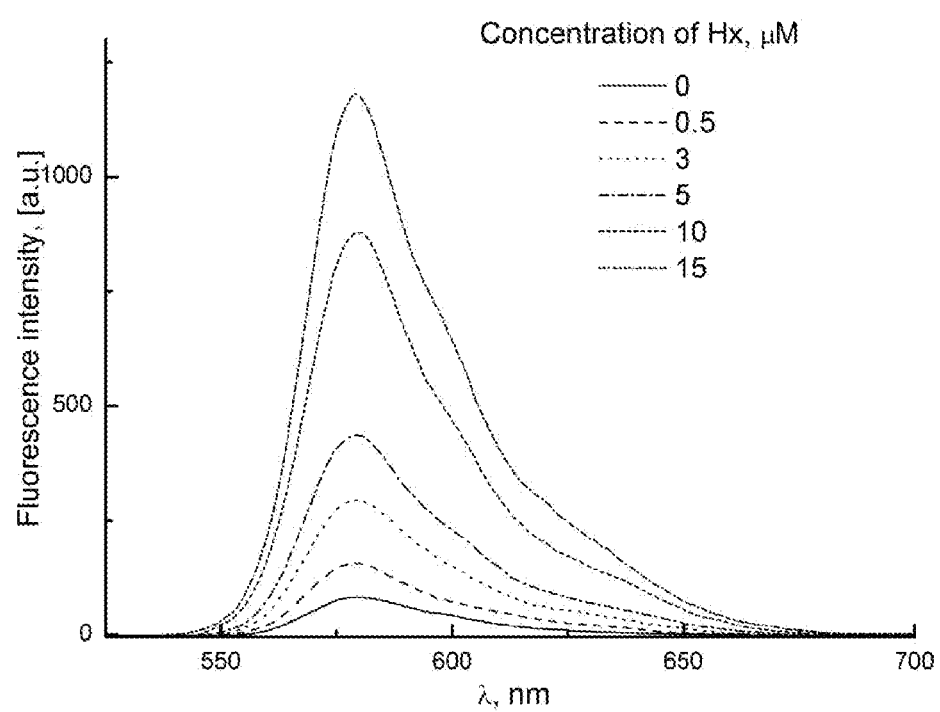

[Fig. 3]
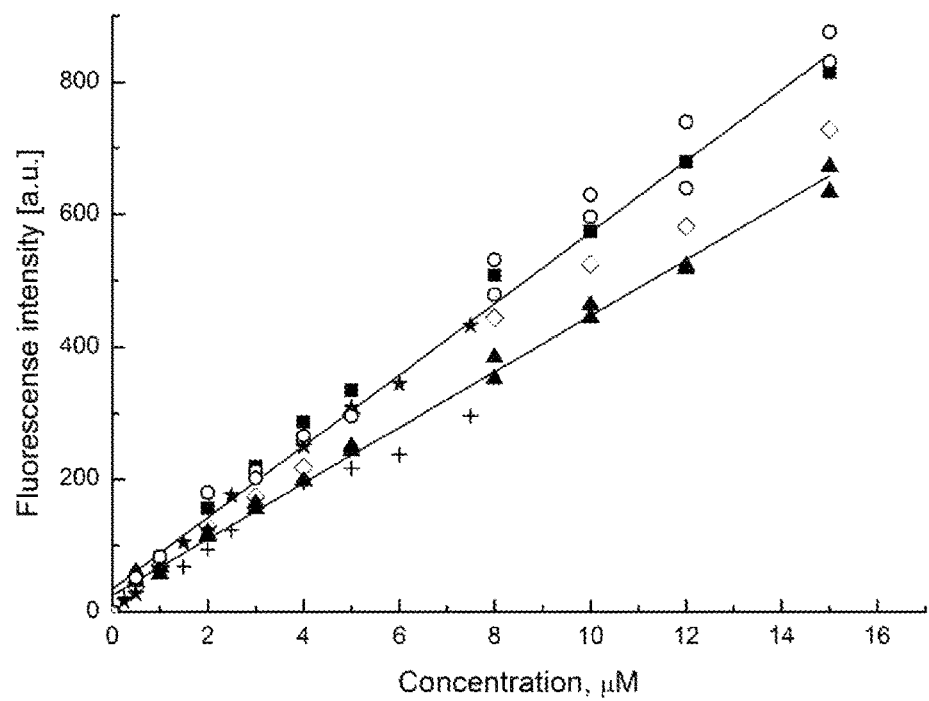

[FIG.4]
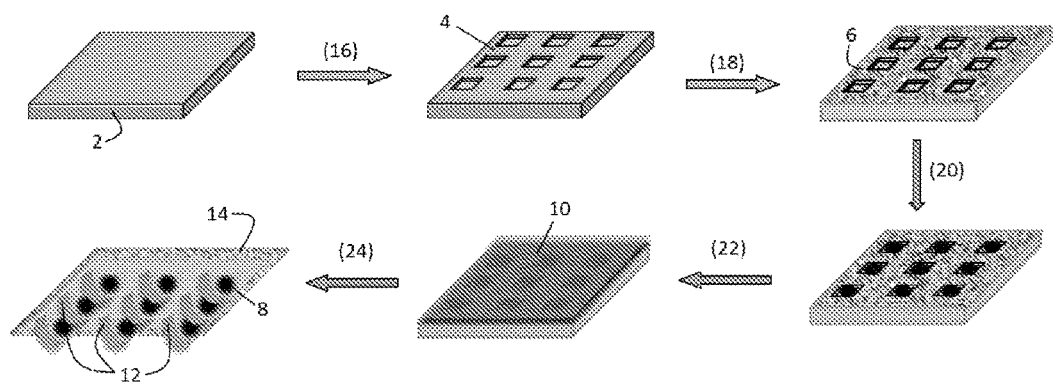

[FIG. 5]
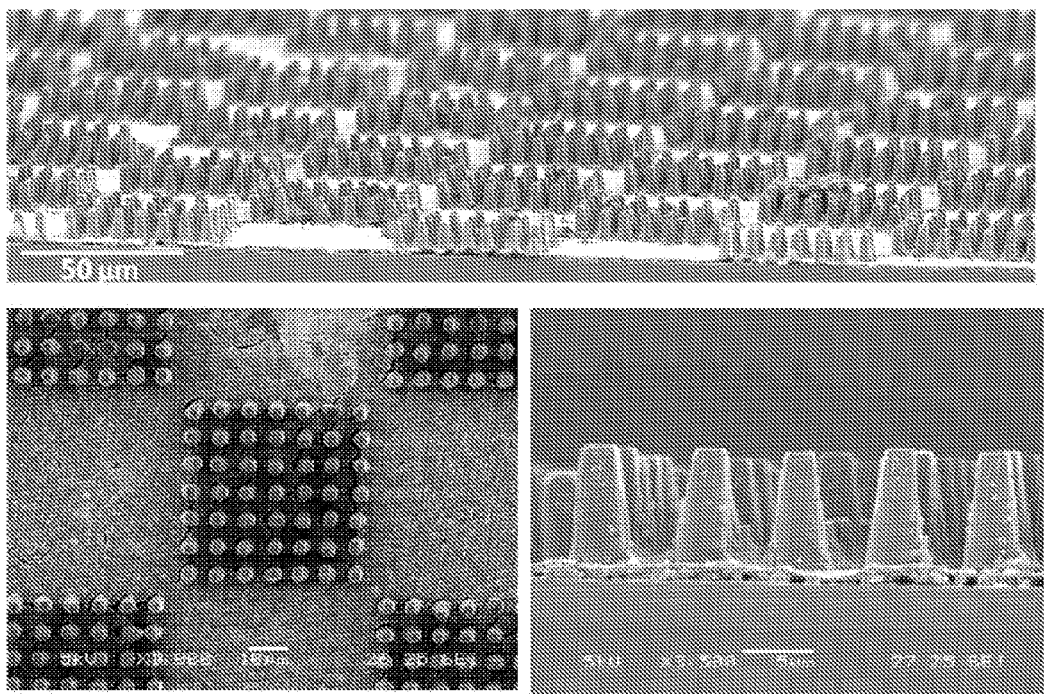

[FIG. 6]
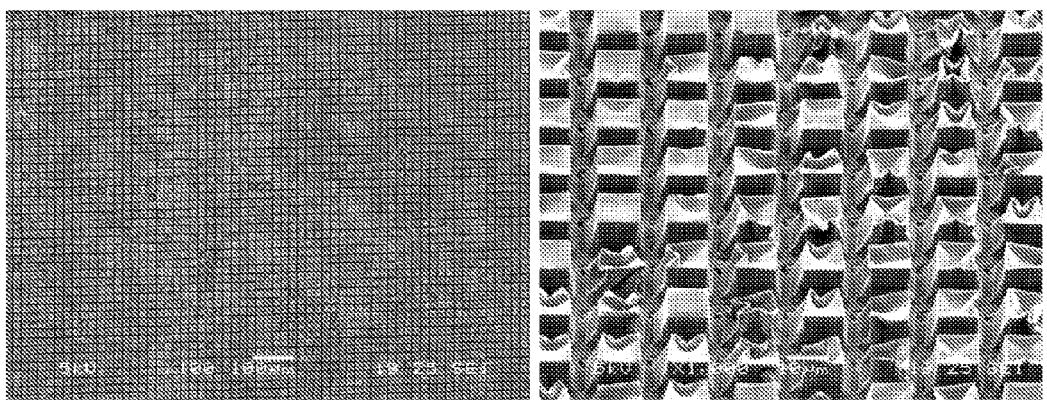

[FIG. 7]
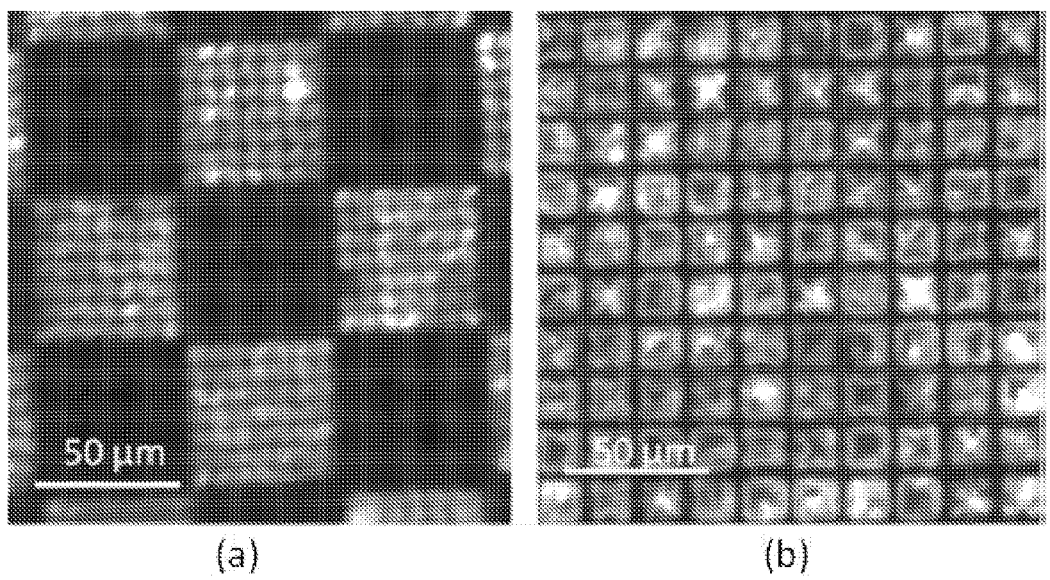
(a)        (b)

[FIG. 8]
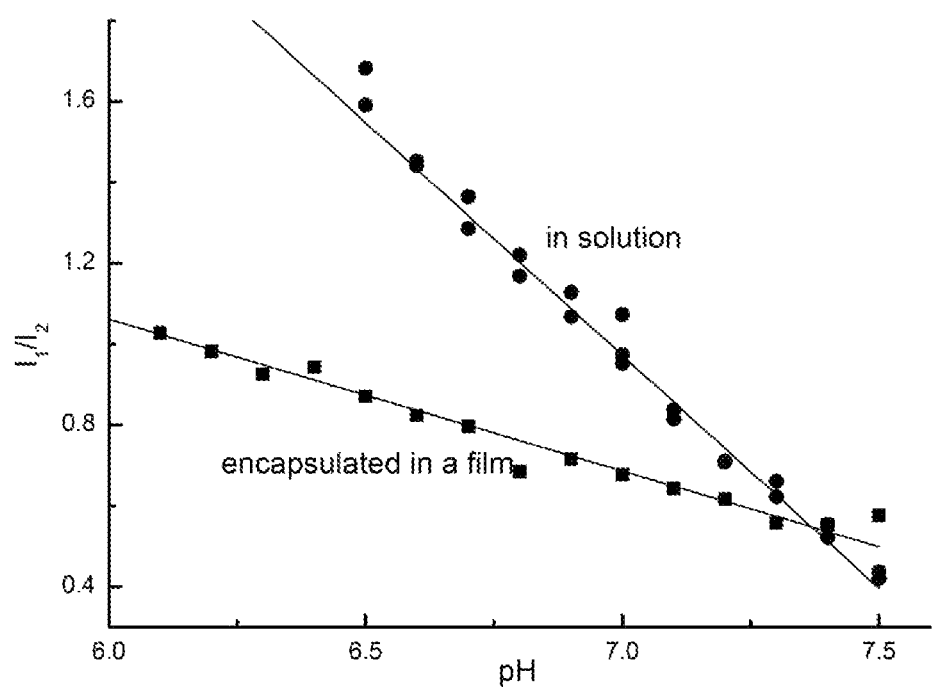

FILM SENSOR

CROSS-REFERENCE TO RELATED APPLICATIONS

This patent application is a National Stage Entry of International Patent Application No. PCT/SG2015/050043, filed on Mar. 19, 2015, which claims the benefit of priority of Singapore patent application No. 10201400820Q, filed on Mar. 20, 2014, the contents of each of which are hereby incorporated by reference in their entirety for all purposes herein.

TECHNICAL FIELD

The present invention relates to a semi-permeable film, its method of fabrication and its uses thereof.

BACKGROUND ART

Food safety within the food industry is of utmost importance as food contamination or deterioration impacts both health (food poisoning) and overall quality (taste and texture) of the food product. Current technologies aim to provide long-lasting freshness of a food product. For example, the primal cuts of chilled, vacuum-packaged beef can have a shelf life of 30 weeks and beyond.

In some countries, there are legal requirements for every basic packaging unit of meat or imported meat products to be labelled. The labels should state, among other details, the date on which the meat product was packed, the shelf life (or its best before date or the expiration date). The indicated dates are usually supported by experimental data but are always averaged. Thus, even if the quality of that food product remains acceptable and safe for consumption after the expiration date, its sale would not be allowed.

On the other hand, whether each product will achieve its shelf life is dependent upon initial quality of the meat (pH, microbiological quality), the integrity of the packaging, the presence of adequate temperature control (minus 0.5±0.5° C.), etc. For meat products that are left unpacked for an extended period after slaughter, even vacuum-packaging may not provide an extended shelf life because of the decline in activity of certain enzymes in the meat which assist the consumption of oxygen present in the packaging head space.

There are generally two types of methods used to evaluate food freshness/spoilage. One is a rapid but expensive and subjective test of the organoleptic attributes. This method becomes less reliable when applied to the inspection of processed food. The other is the detection of certain biomolecules/bio-markers of food spoilage due to autolysis or bacterial growth using chemical assays. This method is time-consuming, destructive and requires sophisticated equipment, highly skilled operators, etc. Both these methods are applied for inspection of some chosen samples from a whole consignment.

These methods are generally suitable for food safety agencies, but may not be suitable for use in supermarkets, consumer homes and may not be applicable towards every form of packaged meat/poultry/seafood ("food products").

There is thus a need for a rapid and non-destructive method of evaluating freshness/spoilage of food products. Preferably, it is desired that the method is capable of inspecting a large number of samples on-site by scanning through the packaged product. Such methods are expected to improve consumer confidence in the food products even if the indicated shelf-life may be close to expiring.

A number of methods/devices have been developed to evaluate freshness and detect spoilage of food products. In general, there are four groups of such methods. The first group is time-temperature indicators. Temperature is an important environmental factor influencing the kinetics of physical and chemical deteriorations, as well as affecting the rate of microbial growth in food products which is pertinent to chilled or frozen food products. Time-temperature indicators report temperature history during transportation and storage. These indicators may change color in response to the intensity of the temperatures the food product was exposed to and the duration of exposure.

Radio-frequency identification technology ("RFID tagging") helps to identify a product, its manufacturing date, country of origin, etc. Temperature monitoring RFID tags have been developed for assessing freshness of food products. These RFID tags have a microchip for sensing temperature changes over time, and recording data throughout the supply chain journey of the food product. At various key points, a prediction of the food product's remaining shelf-life can be made based on the recorded data. Initial product quality may be recorded for each consignment of food product to establish the parameters for the shelf-life prediction.

The second group is gas indicators signalling the gas composition in the package headspace. Of particular prominence are oxygen indicators as it is typically $O_2$ that causes oxidative rancidity, color-changes and also leads to microbial spoilage of foods. Other useful gas indicators may be capable of detecting and measuring water vapor, carbon dioxide, ethanol, hydrogen sulfide, and other gases.

The third group is biosensors that detect and identify pathogens and monitor post-processing food quality parameters. Usually, these biosensors contain a specific-pathogen antibody that can recognize and report the presence of a specific target analyte, e.g., contaminating bacteria.

The fourth group is indicators that report chemical changes within a food product during microbial growth. An increase in pH in meat/poultry/seafood juice upon storage may be the result of the formation and accumulation of biogenic amines due to enzymatic amino acids decarboxylation. Some bacteria which are inhibited at pH 5.4-5.7 can grow to spoilage levels at a higher pH, thus consuming amino acids and producing even more biogenic amines hence further increasing pH in a positive feedback loop. Such biochemical changes occur when spoilage has commenced, and can be indicative of a medium- or a late-stage of the food spoilage process.

K-index measurement is based on measuring ATP breakdown products formed from the initial biochemical processes occurring once an animal or fish has died, but long before spoilage begins. Measurement of the K-index allows anticipation of the beginning of spoilage and to better control the freshness level of the product. K-index can be used as a freshness marker at an early stage of the food spoilage process. Moreover, the K-index also determines the quality of food produce as it also correlates to the major component of the savoury ("umami") taste.

Other detectable metabolites are for instance organic acids such as n-butyrate, L-lactic acid, D-lactate and acetic acid; ethanol; biogenic amines such as histamine, putrescine, tyramine and cadaverine.

However, at this time, known time-temperature indicators, gas sensors or analyte-sensors are unable to provide comprehensive information about the complex biochemical processes occurring in food upon ageing depending on the storage time, temperature, packaging conditions, microbial loading, humidity, etc.

The development of multi-sensors for the quantitative, rapid and concurrent detection of different analytes is one of the major challenges in analytical chemistry.

A majority of existing multi-sensors called "electronic noses" were developed for analysis of gases. More recently, multi-sensors called "electronic tongues" have been developed for liquid analysis through the use of a multivariate interpretation of signals coming from a set of electrodes. Electronic tongues have been applied for food freshness analysis by measuring both pH and K-index. However, these methods require analysing samples obtained from crushed meat or sticking a set of electrodes directly onto a meat product to be tested, i.e., these are destructive methods and assessment cannot be made remotely.

Optical sensing systems can be useful for food freshness/ spoilage assessment as they enable rapid and non-destructive scanning of samples on-site remotely, through the common packaging material. Among optical methods, fluorimetry is a promising analytical tool as it provides high sensitivity and ability for simultaneous detection of multiple-analytes at low cost.

Hence, it has been contemplated to provide optical sensing elements in food packaging material.

For instance, it has been suggested to encapsulate fluorescent dyes in a solid polymer matrix. In particular, the fabrication of such sensors generally involves dissolution of lipophilic sensing dye and an appropriate polymer support in an organic solvent. This solution is then applied to a solid substrate like polyester film or glass and allowed to dry. A number of coating techniques like casting, spin coating, dipping have been used to produce a thin film of dye polymer coating.

In another approach, sensing dyes are absorbed in mesoporous inorganic particles, e.g. silica or alumina. A dye solution in the appropriate solvent, e.g., dichloromethane or ethanol, is added to a suspension of mesoporous particles for 24 h followed by solvent removal. The powder containing 2-8 wt. % of a dye is placed into a microplate which is packed together with meat in polystyrene boxes. In both methods, vapours of an analyte (oxygen or volatile compounds generated during meat spoilage) penetrate the solid matrix through simple diffusion. That is, these sensors work as "optical noses", which analyse and detect the presence of gases and other volatile compounds in the headspace of food packaging.

The drawback of such sensors is that they cannot be applied to packaged foods with insufficient or no headspace, e.g., foods that are vacuum-packed. Also, gas detection (e.g., $CO_2$) is not a comprehensive method of assessing freshness. Such sensors also provide little information as to the extent of food spoilage or the taste quality (e.g., the umami taste) of the food product. Furthermore, by placing these sensors in close proximity to the food product, there is also a risk of contaminating the food products with the chemicals present in these sensors.

Oxygen-sensitive fluorescent dyes have also been indicated for use in sensing applications. In one known example, oxygen-sensitive fluorescent dyes are encapsulated within a polymer matrix that is substantially permeable to oxygen. The polymer matrix is then applied onto food packaging material. The encapsulation process is however not straightforward and there is little control over the amount of dyes that are contained within the polymer matrix. It is further considerably challenging to control the permeability of the polymer matrix.

Accordingly, the methods and sensors discussed above are not adequate for providing a wholesome assessment of food quality or freshness. These techniques are mainly interested in the detection of a particular volatile compound (e.g., amine), or a particular gas ($O_2$ or $CO_2$), or the change in a particular property (e.g. pH). However, these indicators, when individually assessed and measured, may be insufficient for ascertaining the freshness of the food product. For instance, some food may not display an appreciable change in pH despite having undergone spoilage. In such cases, a sensor that is capable of measuring the K-index would be able to detect spoilage way in advance of the pH sensor.

Other techniques for testing food products include, e.g., the use of potentiometric probes or food sample testing via chromatographic techniques e.g., high pressure liquid chromatography ("HPLC"). However, all these techniques suffer from a need to obtain a food samples or otherwise having to destroy the packaging of the food product before testing can be conducted. Such techniques do not permit a consumer prior to purchase or for a retailer to assess the quality/ freshness/spoilage of the product without making the product unsellable.

Accordingly, there is a need to provide a sensor that overcomes or at least ameliorates the disadvantages or drawbacks discussed above. There is further a need to provide a method for making such sensors.

SUMMARY OF INVENTION

In a first aspect of the present disclosure, there is provided a sensor comprising a semi-permeable film layer, said semi-permeable film layer comprising at least one integrally formed well having at least one sensing element disposed therein; wherein the well is sealed by a second film layer, said semi-permeable film layer being impermeable to said sensing element but is permeable to at least one analyte detectable by said sensing element. The analytes may be water soluble or oil soluble analytes.

Advantageously, the second film layer substantially engages with the semi-permeable film layer to seal the one or more integrally-formed wells of the semi-permeable film, thereby encapsulating the sensing element within the wells of the semi-permeable film. The second film layer may be impermeable to the analytes and the sensing element.

In one embodiment, a plurality of wells (or "microcompartments" or "microwells") is integrally-formed on the semi-permeable film layer. The arrangement and shape of the wells are not particularly limited so long as they provide sufficient volume for encapsulating the sensing elements of choice. The arrangement of wells on the semi-permeable film (e.g. size, distribution density, pitch, etc.) can also be configured as necessary to generate a desired output signal (whether captured manually or automatically by a machine). In one embodiment, the array of wells is a highly ordered array, wherein the wells are arranged in a manner to provide sensing elements adapted for detecting particular analytes in designated zones or locations to enable easy signal capture.

The disclosed sensor is capable of assessing the spoilage characteristics of a food product regardless of the cause of spoilage, whether from extended period of storage or violation of the appropriate storage conditions or due to leaking or tampered packaging. Also advantageously, the disclosed sensor does not require direct contact with an analyte to be detected or measured and can be employed in non-destructive or non-contact measurements of various physical/chemical parameters.

Advantageously, the disclosed semi-permeable film may be provided as a thin, flexible layer that can be readily affixed to a substrate, e.g., an interior surface of a food packaging. In particular embodiments, the disclosed sensor may have a total thickness of 10 micron or less taking into account the depth of the wells. Accordingly, the disclosed sensor can be easily incorporated into food packaging without requiring additional packaging space.

More advantageously, the disclosed sensor is able to separately or concurrently detect (whether directly or indirectly) dissolved gases (e.g. $CO_2$ or $O_2$), glucose, and other water/oil-soluble analytes such as metabolite compounds formed by cell autolysis or due to bacterial growth (e.g., hypoxanthine, inosine, etc.). Accordingly, the disclosed sensor provides a comprehensive assessment of food freshness and quality by measuring at least two or more physical or chemical properties, e.g., changes in pH and/or the ratios of the concentrations of respective metabolite analytes (e.g., the measurement of the K-index as an indicator of food freshness and taste).

In one embodiment, the semi-permeable film is a polyelectrolyte multi-layer film ("PEM film") that has been fabricated by a layer-by-layer ("LbL") deposition process. The LbL fabrication process advantageously results in no hazardous by-product being produced and allows precise control over the thickness and porosity of the deposited PEM. Advantageously, the thickness of such PEM films can be controlled to a micron or nano-meter scale.

In one embodiment, the semi-permeable film layer is composed of multiple polyelectrolyte layers wherein oppositely-charged layers are disposed alternately on each other to thereby form a polyelectrolyte multi-layer (PEM). Advantageously, the PEM is permeable to gaseous analytes (e.g., $CO_2$, $O_2$, volatile amines) and water-/oil-soluble analytes but is not permeable to the sensing element encapsulated by the polyelectrolyte film layer. Further advantageously, the use of a PEM film allows the disclosed sensor to separately or concurrently detect gases and chemical or biochemical markers produced during autolysis or by bacterial growth.

In one embodiment, the second film layer (or "sealing layer") is an optically translucent or transparent polymer layer. The second film layer may be a PEM film. The film composition and thickness of the second layer may be the same as or different from the semi-permeable PEM film. In one embodiment, the semi-permeable layer comprising the integrally formed wells is thicker than the second film layer. The PEM film may be shaped like a "micro-bubble wrap film" with a patterned array of sealed wells (or also termed "microcompartments"). Once brought into direct contact with a food sample, the concentration of analytes inside the wells and in the food juice will reach chemical equilibrium, but the encapsulated macromolecular reagents (also termed "sensing elements") will remain trapped within the well.

Yet another advantage of the disclosed sensor rests in the use of the translucent or optically transparent PEM film. The optical properties of the PEM film permits ready observation and measurement of the fluorescence emitted by the sensing elements upon reacting with the target analytes or with by-products (or derivatives) generated by reactions of the analyte compounds.

Still a further advantage of the use of the PEM films for fabricating the disclosed sensor rests in the mechanical strength of such PEM films. The PEM film may comprise one or more non-polyelectrolyte layers such as inorganic fillers. The inorganic fillers may be selected to possess an opposing charge to the polyelectrolyte layers which it is sandwiched between. In one embodiment, the PEM film may be a composite material comprising polyelectrolyte layers and at least one or more layers of clay, calcium carbonate, or other suitably charged filler layer.

Particularly, where the PEM film is a composite material, its mechanical properties (both stiffness and tensile strength) can be adjusted to withstand shear forces and pressure experienced in conditions mimicking the real food transportation. Appropriate fine-tuning of the specific composition of the PEM film and its thickness may be useful to prevent rupturing of the wells and leakage of the sensing elements contained therein.

In one embodiment, the disclosed sensor may contain at least one exposed outer layer that is not substantially engaged with the semi-permeable film layer. Advantageously, the exposed outer layer can be an adhesive layer or may be made adhesive for coupling to or for reversibly engaging with a substrate, e.g., an interior surface of typical packaging material (e.g. polyvinyl chloride, polystyrene and polylactic acid). Still advantageously, the disclosed sensor, and in particular the PEM films, may be biocompatible which makes for easy disposal and additionally prevents or ameliorates the risk of toxic food contamination.

BRIEF DESCRIPTION OF DRAWINGS

The invention will be better understood with reference to the detailed description when considered in conjunction with the non-limiting examples and the accompanying drawings, in which:

FIG. 1a shows emission spectra of SNARF-1 dextran dye (0.05 mg/mL in phosphate buffer) depending on the solution pH, excitation wavelength 530 nm.

FIG. 1b shows emission spectra of SNARF-4F dye (5 μg/mL in phosphate buffer) depending on the solution pH, excitation wavelength 550 nm.

FIG. 1c is a graph showing the ratios between emission intensities I585/I630 depending on the pH for SNARF-1 and SNARF-4F.

FIG. 2 shows an emission spectra of Amplex®UltroxRed dye formed in cascade enzymatic reactions in system containing Amplex®UltraRed (50 μM), horseradish peroxidase ("HRP") (3.6 Units/mL), XOD (0.15 Units/mL), NP (2.5 Units/mL), phosphate buffer at pH 5.5, and different concentrations of Hx in the range from 0 to 15 μM. Excitation wavelength was 500 nm.

FIG. 3 is a graph showing the intensities of emission at 585 nm (after subtraction the intensities of self-oxidized Amplex®UltroxRed) obtained for the solutions of sensing element III containing pure Hx (represented by square data points), Ino (represented by circular data points), and IMP (represented by triangular data points) as well as the mixed solution of Hx+Ino+IMP (represented by diamond data points) and for the solution of sensing element IV containing the mixed solution of Hx+Ino+IMP (represented by star data points). Symbols represented by cross (+) data points indicate difference between the emission intensities in mixed solutions of Hx+Ino+IMP measured in elements III and IV. Excitation wavelength was 500 nm.

FIG. 4 shows a simplified schematic overview of a process fabricating a sensor according to the present invention.

FIG. 5 are SEM images of a $(PAH-PSS)_{40}/(PDADMA-PSS)_8$ film of pattern (I) sealed onto a silicon substrate. The subscript indicates number of polyelectrolyte layers FIG. 6 are SEM images of the (PAH-PSS)$_{40}$/(PDADMA-PSS)$_8$ film of pattern (II) sealed onto a silicon. The subscript indicates number of polyelectrolyte layers.

FIG. 7 shows fluorescence microscope images of the (PAH-PSS)$_{40}$/(PDADMA-PSS)$_8$ films of patterns I (a) and II (b) sealed onto a glass. The wells of both films were loaded with sensing element I.

FIG. 8 is a graph showing ratios of emission intensities $I_{585}/I_{630}$ depending on the pH for SNARF-1 dextran (sensing element I) free in a solution (represented by circular data points) and encapsulated in a film of pattern I (represented by square data points) by a second approach.

DEFINITIONS

The terms "sensing element(s)", "sensing reagent(s)" or "reagent(s)" may be used interchangeably in the present specification to refer to a chemical compound or substance or group of substances which is capable of detecting or is responsive to the presence of one or more target analytes. The detection step may optionally involve chemical reaction between the analyte and the sensing element or a derivative of the analyte with the sensing element.

The term "integrally formed", when used in the present specification to refer to wells formed on a semi-permeable film, is taken to mean that the wells and the semi-permeable film are formed from or of a single or unitary structure. In an exemplified embodiment, the wells are formed by imprinting a polymer substrate (e.g. PMMA) with a patterned mold to create a negative replica of the mold comprising well formations. Subsequently, a semi-permeable film is deposited on the imprinted polymer substrate to thereby form the semi-permeable film layer having integrally formed wells.

The term "polyelectrolyte", as used in the present specification, is taken to refer to polymers having, in its repeating monomer unit(s), at least one electrolyte moiety (a moiety that forms a charged group when dissolved in an ionizing solvent e.g., water) or a charged species. Such polymers may include block polymers, co-polymers, and/or statistical polymers. Polyelectrolytes may include polyacids, polyampholytes, polycations, polyanions, conjugated or non-conjugated polymers.

The term "polyelectrolyte multilayers" or "PEM", when used in the present specification, may refer to coatings or films which are fabricated using layer-by-layer (LbL) deposition or layer-by-layer adsorption techniques. During the deposition process, polymer layers exhibiting opposing surface charges are deposited alternately on top of each other in a multi-layer configuration. Thus, the PEM coating or film may exhibit intermolecular, inter-layer bonding through electrostatic attractions, Van Der Waals and/or hydrogen bonding. The term PEM film may also refer to composite multi-layer structures wherein one or more polyelectrolyte layers have been substituted with a correspondingly charged species (e.g., inorganic fillers, such as surface-modified nanoparticles, clay, calcium carbonates, etc.). There is generally no particular limitation to the total number of layers to be provided in a PEM film, which is dependent on the desired thickness and/or permeability to be achieved.

The word "substantially" does not exclude "completely" e.g. a composition which is "substantially free" from Y may be completely free from Y. Where necessary, the word "substantially" may be omitted from the definition of the invention.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

DESCRIPTION OF EMBODIMENTS

In a first aspect, the present invention relates to a sensor comprising a semi-permeable film layer, said semi-permeable film layer comprising at least one integrally formed well having at least one sensing element disposed therein; wherein the well is sealed by a second film layer, said semi-permeable film layer being impermeable to said sensing element but is permeable to at least one analyte detectable by said sensing element.

The semi-permeable film layer may comprise at least two or more polyelectrolyte layers, wherein oppositely charged polyelectrolyte layers are deposited alternately on each other. In one embodiment, the semi-permeable film layer is a polyelectrolyte multilayer (PEM) film.

For instance, if the initial polyelectrolyte layer is a polyanion or a negatively charged layer; it is followed by a polycation or a positively charged layer, and which is further followed by a oppositely charged layer, and so forth; and vice versa. Furthermore, in certain embodiments, at least one or more polyelectrolyte layers may be substituted by an appropriately charged medium, e.g., micro- or nanoparticles or layers with other types of interaction, e.g. formed by hydrogen forces, or specific binding. In certain embodiments, at least one or more layers comprised within the PEM is cross-linked. The crosslinking may comprise formation of inter-/intra-layer covalent bonds or ionic bonds.

The PEM may comprise nano-sized polyelectrolyte layers, e.g., about 1 nm thick. The PEM may comprise alternating organic and inorganic layers, e.g., clay-polyelectrolyte multilayers. In one embodiment, the PEM structure comprises clay and a polyelectrolyte poly(diallyldimethylammonium chloride) or "PDADMA", where the PEM structure comprises about 200 bilayers and has a thickness of about 5 micrometers. Such clay-polyelectrolyte structures may have a tensile strength of $\sigma=(100\pm10)$ MPa, and Young's modulus, $Y=(11\pm2)$ GPa. Such structures are disclosed in *Nature Materials*, 2, 413-418 (2003), the contents of which are hereby incorporated by reference.

The PEM structure may comprise alternating layers of a clay and a polyelectrolyte layer that has been conjugated with at least one amino acid e.g., lysine. The amino acid may be optionally grafted or modified with a polyether, e.g., a polyethylene glycol. The polyelectrolyte layer may be cross-linked. In one embodiment, the PEM comprises alternating layers of Na$^+$ montmorillonite clay and L-3,4-dihydroxyphenylalanine Lys-PEG. The L-3,4-dihydroxyphenylalanine Lys layer may be cross-linked, e.g., with $Fe^{3+}$. The PEM structure may comprise 50 bilayers having a thickness of about 1.2 micron in total. Such PEM structures may display tensile strength of $\sigma=(200\pm30)$ MPa, and Young's modulus, $Y=(7\pm1)$ GPa. Such PEM structures are disclosed in *Adv. Mater.*, 19, 949-955 (2007), the contents of which are hereby incorporated by reference.

In another embodiment, the PEM structure comprises alternating Na+ montmorillonite clay and poly(vinyl alcohol) layers. The PEM structure may comprise from about 200 to 300 bilayers and a thickness of about 1 to 1.5 micron. The PEM structure may be treated with glutaraldehyde. Such PEM structures may display tensile strength of $\sigma=(400\pm40)$ MPa, and Young's modulus, $Y=(106\pm11)$ GPa. Such PEM structures are disclosed in *Science*, 318, 80, (2007), the contents of which are hereby incorporated by reference.

In yet another embodiment, the PEM structure may comprise polyelectrolyte multilayers impregnated by an inorganic compound, e.g., calcium carbonate. The chemical filtration of such inorganic compounds or additives may be from 10 to 80% w/w into pre-fabricated PEMs. In one embodiment, there is provided a 40-60 bilayer poly(sodium 4-styrenesulfonate)-poly(diallyldimethylammonium chloride) multilayer that has been impregnated with $CaCO_3$ at about 60% w/w. Such PEM structures may have a Young's modulus of about 10±0.3 GPa and an average hardness of 6.3±0.3 GPa. In other embodiments, the impregnation of the inorganic compound to the PEM structure may be from about 10%, 20%, 30%, 40%, 50%, 60%, 70%, or 80% by weight.

The semi-permeable layer may also be composed of other forms of porous material having the appropriate molecular weight cut off, i.e., not permeable to the sensing elements but permeable to at least one analyte to be detected by the sensing elements. For example, the semi-permeable layer may be made of cellophane, regenerated cellulose or cellulose ester; polysulfone, polyethersulfone, etched polycarbonate, collagen etc.

The number of polyelectrolyte layers may be adjusted to achieve a desired thickness, permeability, flexibility and/or hardness. The semi-permeable film layer may comprise from 2 to 200 polyelectrolyte layers. In embodiments, the semi-permeable film layer may contain 10, 20, 30, 40, 50, 60, 70, 80, 90, 100, 110, 120, 130, 140, 150, 160, 170, 180, 190 or 200 alternating layers. In embodiments, the semi-permeable film layer may contain 2, 4, 6, 8, 10, 12, 14, 16, 18, 20, 22, 24, 26, 28, 30, 32, 34, 36, 38, 40, 42, 44, 46, 48, 50, 52, 54, 56, 58 or 60 alternating layers. In a particular embodiment, the semi-permeable film layer comprises 40 alternating layers of poly(sodium 4-styrene sulfonate) ("PSS") and poly(allylamine hydrochloride ("PAH"). One or more layers of polyelectrolyte layers may be provided as an anchoring layer. The choice of anchoring layer may depend on the surface charge of the template on which the polyelectrolyte layers are to be deposited thereon. In one embodiment, the layer-by-layer deposition is performed on a PMMA substrate (which is negatively charged). Thus, a suitable polycation layer (e.g. PEI) may be used as a base/anchoring layer in such embodiments. The number of layers may vary depending on the choice of polyelectrolytes, the geometry of microwells, etc.

The polyelectrolytes may be advantageously selected to be food-grade polyelectrolytes and natural polyelectrolytes. Exemplary food-grade or natural polyelectrolytes may be selected from, but are not limited to, the group consisting of: sodium polyalginate, poly-L-lysine, poly-L-arginine, chitosan, carboxy-methyl cellulose, proteins, tannins, DNA, RNA, etc.

The polyelectrolytes may also be selected from the group consisting of: poly(acrylic acid), polyallylamine hydrochloride (PAH), polystyrene sulfonate (PSS), polyethyleneimine (PEI), N-dodecyl, methyl-poly(ethyleneimine), co-polymers, and block co-polymers thereof. The PEM may also comprise one or more intermediate layers of inorganic fillers, e.g., $CaCO_3$, clays to improve mechanical properties.

The semipermeable film may have a thickness from about 100 nm to about 2 µm. It may be generally desirable to provide a thickness sufficient to provide mechanical strength and to ensure structural integrity of the film. The film is intended to be sufficiently flexible for conforming to a surface contour of a substrate to which the film may be coupled to.

The thickness of the film may be selected as appropriate for permitting rapid and efficient diffusion of analytes into the wells. The thickness of the film may also be suitably adjusted so that amount of film material in contact with the food is kept to a trace level. Typical thickness of the film may be from about from 100 nm to 1000 nm, from 100 nm to about 900 nm, from about 100 nm to 700 nm, from 100 to 500 nm, from 100 to 300 nm, or from 100 to 200 nm Advantageously, the Young's modulus of a PEM film as disclosed herein may be from about 1 GPa to 150 GPa. 1 GPa to 125 GPa, from about 1 GPa to 100 GPa, from about 1 GPa to 80 GPa, from about 1 GPa to 60 GPa, from about 1 GPa to 40 GPa, from about 1 GPa to 20 GPa, from about 1 GPa to 10 GPa, from about 1 GPa to 5 GPa, from about 5 GPa to about 150 GPa, from about 5 GPa to about 125 GPa, from about 5 GPa to about 50 GPa, from about 5 GPa to about 80 GPa, from about 5 GPa to about 60 GPa, from about 5 GPa to about 40 GPa, from about 5 GPa to about 20 GPa, from about 5 GPa to about 10 GPa, from about 10 GPa to about 150 GPa, from about 10 GPa to about 125 GPa, from about 10 GPa to about 100 GPa, from about 10 GPa to about 80 GPa, from about 10 GPa to about 60 GPa, from about 10 GPa to about 40 GPa, or from about 10 GPa to about 20 GPa. In one embodiment the composite PEM structure is a $CaCO_3$/PEM composite having a Young's modulus of about 10 GPa. In other embodiments, clay/PEM composite structures may possess a Young's modulus of about 125 GPa.

Advantageously, the tensile strength of a PEM film as disclosed herein may be from about 10 MPa to about 40 MPa, from about 20 MPa to about 40 MPa, or from about 30 Pa to 40 MPa, which is comparable to typical plastics like high density polyethylene.

The tensile bond strength between the semi-permeable film layer and the second sealing layer may be from as high as 1 MPa, 2 MPa, 3 MPa, 4 MPa, 5 MPa, 6 MPa, 7 MPa, 8 MPa, 9 MPa, or 10 MPa. Advantageously, this ensures that the contents of the microwells would be securely encapsulated and would not contaminate any food material the sensor comes into contact with.

The semi-permeable film layer may comprise an array of integrally formed wells, wherein at least one sensing element or a plurality of sensing elements is encapsulated in each well. The array can be an ordered array or a dis-ordered arrangement where the wells are distributed randomly over the surface of the semi-permeable film layer. The wells may assume various shapes and configurations. For example, the wells may be conical, pyramidal shaped, truncated square pyramids, rectangular shaped, cuboidal, etc. Wells containing the same sensing elements may be grouped to form a cluster of wells. Such well clusters may be separated spatially on the semi-permeable film layer to provide ease of observation and/or signal capture.

The wells may contain a singular sensing element or a mixture of sensing elements. The sensing elements may be provided as a solid, a dispersion or a solution. At least one well in the array of wells may contain a singular sensing element or a mixture of at least two distinct sensing elements, which is/are adapted to detect the presence of at least one or more analytes. In one embodiment, the mixture of sensing elements is adapted to concurrently detect one or more, two or more, or three or more analyte compounds which are the products of cell autolysis or are products of bacterial metabolism.

The sensing elements may provide at least one measurable property or output signal upon detecting the analytes or their derivative compounds. The measurable property may be an optical property, e.g., colour, fluorescence, etc.

Where a mixture of sensing elements is provided in a well, the mixture may output a single signal or multiple signals. Where multiple signals are produced, ratio-metric measurements may be taken to determine the respective concentrations of each detected analyte compounds.

Exemplary analytes desired for detection may be selected from the group consisting of: H+ ions, hypoxanthine, inosine, inosine monophosphate, n-butyrate, L-lactic acid, D-lactate, acetic acid, ethanol, and biogenic amines (e.g., histamine, putrescine, tyramine and cadaverine). Other analytes suitable for detection may include oxygen and glucose. The temperature profile of the food may also be continuously monitored by temperature sensing elements.

In one embodiment, the disclosed sensor may detect the concentration of analytes selected from the group consisting of: hypoxanthine, inosine and inosine monophosphate.

Suitable sensing elements for detecting these analytes are known to a skilled person and shall not be discussed in detail. In embodiments, the sensing elements are macromolecular structures that are incapable of passage through the semipermeable film or the PEM. The sensing elements disclosed herein may be selected from the group consisting of: fluorescent dyes and enzymes. An example of a commercially available reagent is Amplex®UltraRed (marketed by Life Technologies). Specifically, such sensing elements may be sensitive to a reaction by-product (e.g., hydrogen peroxide $H_2O_2$) formed in a reaction cascade involving these analytes. Advantageously, determining the concentrations or relative concentrations of these analytes allow for the measurement of the K-index, which in turn informs one regarding the freshness, and/or taste quality of a particular food product.

In an embodiment of the disclosed sensor, there is provided concurrently, one or more wells containing sensing elements capable of detecting a change in pH; and one or more wells containing sensing elements capable of detecting the presence of hydrogen peroxide.

The molecular weight cut-off (MWCO) of the semipermeable film or of the PEM layer may be about 5 kDa. Similarly, the MWCO is not particularly limited and may be selected in accordance with the sensing element to be used in the wells and the analytes which are intended for detection. In exemplary embodiments, the MWCO of the semipermeable film layer may be in the range of several kilo Daltons (kDa), e.g., from 1 to 20 kDa, from 1 kDA to 5 kDa, from 1 kDa to 10 kDa, from 1 kDa to 15 kDa, from 5 kDa to 10 kDa, from 5 kDa to 15 kDa, from 5 kDa to 20 kDa, from 10 kDa to 15 kDa, from 10 kDa to 20 kDa or from about 10 to 15 kDa. The MWCO may be variable depending on the pH or temperature conditions which the sensor is exposed to.

The second film layer may be optically translucent or transparent. Advantageously, this allows the output signals to be easily detected by a detection means, e.g., an optical reader or a sensor machine. For instance, it is envisioned that these signals could be picked up on a conveyor belt equipped with appropriate optical detection systems to thereby identify food products whose quality may have been compromised.

The second film layer may comprise or is composed of an adhesive material. In one embodiment, the second film layer is also a polyelectrolyte multilayer. The second film layer may be thinner than the semi-permeable film layer comprising the array of wells. The second film layer may be a PEM coating having from 2 to 20 alternating layers. In embodiments, the second film layer may be an alternating PEM layer having 2, 4, 6, 8, 10, 12, 14, 16, 18 or 20 polyelectrolyte layers. The thickness of the second film layer may be suitably selected to maintain optical translucency or transparency while providing sufficient adhesion and mechanical strength.

The second film layer may comprise a base polymer or polyelectrolyte layer that substantially engages with a top surface of the semi-permeable film layer to thereby seal and encapsulate the sensing elements disposed in the wells. The base polyelectrolyte layer of the second film layer may be oppositely charged to the top surface of the semi-permeable film layer. The semi-permeable film layer and the second film layer may be coupled via intermolecular interactions and electrostatic interactions. The tensile bond strength may be at least 5 MPa or greater. The second film layer may be impermeable to the sensing element but is permeable to gases and other water soluble analytes as disclosed herein.

It is preferred that the second film layer comprises at least one exposed surface that is not substantially engaged with or in direct contact with the semi-permeable film layer. The exposed surface may be adhesive or comprise attachment means for adhesion onto a substrate surface, e.g., an adhesive. The exposed surface may be substantially flat to facilitate ease of adhesion and to increase the contact surface area. In other embodiments, the exposed surface may be directly contacted with or coupled to a substrate without providing any additional adhesive means. Advantageously, the adhesive property may arise from the presence of a large number of mobile, charged groups or moieties on the exposed surface of the second film layer. Accordingly, in one embodiment, the exposed surface of the second film layer is inherently adhesive. The second film layer may also be a gel-like film, which enables it to conform to a surface contour of the substrate. The substrate may be an interior surface of a food packaging material. This attachment would advantageously allow the disclosed sensor to come into direct contact with the fluids or juices of the food product. In this case, the analytes or gaseous analytes may pass into the wells of the sensor by diffusing through the semipermeable wells or the polyelectrolyte layers. However, the sensing elements would not be able to pass through the semipermeable wells, thereby preventing the contamination of the food products. The total thickness of the sensor, which includes the semipermeable film layer and the second sealing layer may be from about 5 to about 50 micron, 5 to 40 micron, 5 to 30 micron, 5 to 20 micron, 5 to 10 micron, 10 to 50 micron, 10 to 40 micron, 10 to 30 micron, or 10 to 20 micron. In one embodiment, the total thickness of the sensor is about 10 micron.

Accordingly, in another aspect of the present invention, there is provided a method of assessing food quality in packaged food, the method comprising the steps of: a) contacting a sensor as disclosed herein with said packaged food; and b) detecting an output signal from the sensor.

In one embodiment, the method may comprise disposing the sensor on an interior surface of food packaging to cause contact between said packaged food and the wells of the sensor. The food packaging is preferably translucent or transparent to permit detection of an optical signal emitted by the sensor.

In still another aspect, there is provided the use of a sensor as disclosed herein for detecting spoilage in a food product. In one embodiment, the sensor is used to detect the presence of particular analytes, or derivatives/reaction products of such analytes which are produced during food spoilage. Additionally, the sensor may also be used to detect or physical/chemical changes, e.g., pH changes, in a food product which are undergoing spoilage.

In yet another aspect, there is provided a method of making a sensor as disclosed herein, said method comprising the steps of: i) depositing a first semi-permeable coating on a patterned template to thereby form a semi-permeable film having at least one integrally formed well; ii) disposing one or more sensing elements in said well; iii) encapsulating said sensing elements in said well; wherein said semi-permeable film is not permeable to said sensing element but is permeable to at least one analyte detectable by said sensing element. In embodiments, the semi-permeable film layer is a PEM film.

In embodiments the encapsulating step may comprise engaging a second film layer with said semi-permeable layer to thereby seal the well and confine the sensing element therein. The second film layer may be deposited directly on the semi-permeable film. Alternatively, the second film layer is fabricated on a plastic substrate or packaging material and thereafter pressed onto the semi-permeable film.

An exemplary method of fabricating the sensor as disclosed herein shall now be discussed with reference to FIG. 4. As a the first step, an array of micro-wells is fabricated on the surface of a free-standing poly(methylmethacrylate) ("PMMA") substrate 2 by imprinting technology 16. For this application, two different patterns of master silicon molds were used: an array of blunted cones 9 µm tall, with 5 µm diameter of the larger base and smaller base shaped as a square having 3 µm edge, the pitch size was 2 µm ("pattern I"); an array of 10 µm tall truncated square pyramids, having larger and smaller base edges of 14 and 10 µm, respectively, and 2.5 µm pitch size ("pattern II"). Both molds were purchased from Eulitha AG, (Switzerland). The imprinting 16 was performed with Obducat imprinter at 140° C. and a pressure of 4 MPa producing a negative replica of the molds on the surface of the PMMA substrate 2. An array of wells 4 is thereby integrally formed on the surface of the PMMA substrate 2 (hereafter known as the "template").

Thereafter, this template is coated with polyelectrolyte multilayers (PEMs) via a Layer-by-Layer (LbL) deposition method (18) using a dip-coating robot machine (Riegler & Kirstein GmbH, Germany) to thereby form a polyelectrolyte multilayer film 6.

Adsorption of all polyelectrolyte layers was performed from sodium chloride (NaCl) solutions of ionic strength 2M, polymer concentration 2 mg/mL, pH ~5.5, 15 minutes and 1 min for each adsorption and DI water washing step, respectively. Prior to dip-coating, imprinted PMMA sheets were sonicated in water for 5 minutes to remove air bubbles that may be trapped inside the wells 2.

Since the PMMA substrate surface is negatively charged due to the presence of uniformly distributed carboxylate groups. So it was first exposed for 15 minutes to branched PEI solution (with pH adjusted to 5.0 using 1M HCl) in order to generate a first anchoring polyelectrolyte layer comprising a high density of positive charges. This was followed by depositing 40 alternating layers of poly(sodium 4-styrene sulfonate) (PSS) and poly(allylamine hydrochloride) (PAH). The polyelectrolyte multilayer film 6 is then washed three times to remove all non-adsorbed macromolecules. The terminal layer was PSS.

In the third step, sensing elements 8 (such as those disclosed herein) were loaded (20) into the wells 2 by two different approaches.

In a first approach, porous $CaCO_3$ microparticles with absorbed sensing elements were synthesized as follows: 100 µL of 1M $Na_2CO_3$ and $CaCl_2$ solutions were injected one by one into 3.8 mL of water solution of a sensing element under vigorous agitation. The resultant 2-3 µm $CaCO_3$ particles were centrifuged and washed 2 times with DI water. The aqueous dispersion of colloid particles with absorbed sensing elements was allowed to move slowly in a 50 µm-thick space layer confined between the imprinted and PEM-coated PMMA substrate and a glass. As the rear front of the liquid dispersion moves, the capillary forces exerted on this interface drag colloid particles across the surface until they are physically trapped by the wells. The maximal number of particles in a well depends on the ratio of the well dimensions to the diameter of the particles.

In a second approach, an aqueous solution of a sensing element was introduced on top of the imprinted and PEM-coated PMMA substrate and allowed to dry. Upon drying, the aqueous solution splits into a number of pools-in-wells and further drying leaves the sensing element precipitate in each well. The PEM film in-between the wells is optionally removed mechanically by wiping with a tissue paper.

In the fourth step, the wet PEM-coated PMMA template housing sensing elements was pressed (22) onto a substrate pre-coated with an adhesive PEM multilayer 10 in a pressurized chamber at 1 MPa and 30° C. for 60 min to thereby seal and encapsulate the sensing elements 8 within the wells 4. Adhesive PEM multilayer 10 comprises eight alternating layers of PDADMA and PSS, which were deposited on a substrate as described above. The terminal layer was PDADMA.

In the fifth step, the PMMA template 2 was removed (24) with tweezers or dissolved in toluene revealing arrays 12 of wells loaded with sensing elements. If porous $CaCO_3$ microparticles were used, they were dissolved in 1M solution of disodium salt of ethylenediaminetetraacetic acid (EDTA). The resulted films were stored under water at room temperature.

SEM and Fluorescent microscope images of the sensor films are shown in FIGS. 5-7. The films are effectively sealed onto a substrate and have arrays of microcompartments/wells of different sizes, shapes and arrangements protruding from on the opposing surface not contacted with the substrate. All wells are thus loaded with fluorescent dyes, although the dye content varies from one compartment to another.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXAMPLES

Materials and Methods

Sensing element I is a commercially available pH-sensitive fluorescent dye SNARF-1 conjugated dextran. FIG. 1a shows emission spectra of this dye (0.5 mg/mL in phosphate buffer) depending on the pH of the buffer. There are two emission bands in the spectra having maximum at 585 and 630 nm, respectively. Emission at 630 nm enhances while emission at 585 nm diminishes upon pH increase having an isosbestic point at 600 nm. The ratio between both signals $I_{585}/I_{630}$ was calibrated as shown in FIG. 1c. It decreases linearly with pH increase from 6.0 to 7.7. Thus SNARF-1 dextran can report pH change in this range with accuracy 0.03 pH unit.

Sensing element II is another commercially available pH-sensitive fluorescent dye SNARF-4F. FIG. 1b shows emission spectra of this dye (13 μg/mL in phosphate buffer) depending on the pH of the buffer. Again, there are two emission bands in the spectra having maximum at 585 and 630 nm, respectively. Emission at 630 nm enhances while emission at 585 nm diminishes upon pH increase having an isosbestic point at 610 nm. The ratios between both signals $I_{585}/I_{630}$ were calibrated as shown in FIG. 1c, it decreases linearly while pH increases from 5.5 to 6.5. Thus SNARF-4F can report pH change in this range with accuracy 0.02 pH unit.

Sensing element III—commercially available reagent Amplex®UltraRed (50 μM), horseradish peroxidase (HRP, 3.6 Units/mL), xanthine oxidase (XOD, 0.15 Units/mL), nucleoside phosphorylase (NP, 2.5 Units/mL).

Sensing element IV—Amplex®UltraRed (50 μM), HRP (3.6 Units/mL), XOD (0.15 Units/mL), NP (2.5 Units/mL), alkaline phosphatase (AP, 90 Units/mL).

K-index is defined as a ratio of combined concentrations of hypoxanthine ("Hx") and inosine ("Ino") [Hx+Ino], to the combined concentrations of Hx, Ino and inosine 5'-monophosphate disodium salt ("IMP"), [Hx+Ino+IMP]. The following sensing elements have been suggested for simultaneous fluorimetric detection of [Hx+Ino] (sensing element III) and [Hx+Ino+IMP] (sensing element IV)

The following cascade enzymatic reactions occur in sensing elements III and IV:

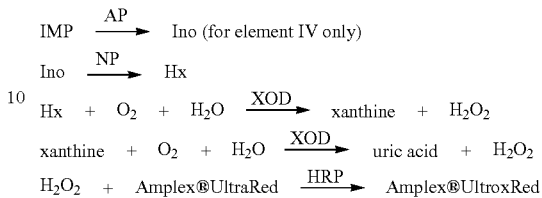

Hydrogen peroxide evolved in the cascade enzymatic reactions oxidizes Amplex®UltraRed producing a highly fluorescent dye. FIG. 2 shows the typical emission spectra obtained from solutions containing different concentration of Hx in phosphate buffer (pH 5.5). Intensity of the emission band at 585 nm increases upon increase of Hx concentration.

FIG. 3 shows the calibration curves for pure Hx, Ino and IMP solutions as well as mixed solutions (Hx+Ino) and (Hx+Ino+IMP) obtained after subtraction of the intensity of selfoxidized Amplex®UltroxRed.

Calibration data for both pure Hx and Ino solutions fall into a single line with a slope of 54±1 μM$^{-1}$ for the whole range of studied concentrations. The data for mixed (Hx+Ino+IMP) solution measured with sensing element III (which doesn't sense or detect IMP) fall into the same line. However the data for pure IMP solution fall into a line with a smaller slope of 42±0.6 μM$^{-1}$. As a result, data for mixed (Hx+Ino+IMP) solution measured with sensing element IV fall in-between of the two lines.

Lower sensitivity of sensing element IV towards IMP could be attributed towards a lower activity of alkaline phosphatase enzyme at the chosen pH 5.5. Nevertheless, the obtained calibration curves for both systems are sufficient to determine the K-index. The combined concentration [Hx+Ino)] can be measured directly with sensing element III. Then one can subtract the emission intensity obtained from sensing element III from the intensity obtained from sensing element IV as shown in FIG. 3. The resulted intensity (i.e., a measured property) can be converted to concentration of IMP using the corresponding calibration curves. Stability of signals from both sensing elements III and IV was checked upon storage at 4° C. The standard deviation remains within 8% over 5 and 3 weeks for sensing elements III and IV, respectively. It increases to 14% for sensing element IV after four and five weeks of storage.

Example 1

Evaluation of Freshness of Meat (Fish) by Sensing Elements I-IV

Fish samples (mid-sized Red Tilapia) weighing 400±50 g were stored on ice and at 5° C. over two weeks. Fish juices were obtained from 2 g of fish fillet by grinding with equal weight volume of water followed by deep freezing at −80° C. After defrosting, samples were centrifuged at 14,000 rpm for 10 min and clear supernatants were used for further analysis. Specifically, the pH was tested by sensing element I. K-index was measured by injecting 300 μL of fish juices in 2.7 mL phosphate buffer solutions at pH 5.5, containing sensing elements III or IV. Colony forming units (CFU) analysis was performed using cultivable plate count assay.

The combined data are shown in Table 1, which shows the results of chemical and biochemical analysis in fish (Red Tilapia) extracts as the function of storage time and temperature.

TABLE 1

| Temperature, ° C. | Storage time, days | [Hx + Ino], μmole/g | [IMP], μmole/g | K-value, % | Counts, CFU/g | pH |
|---|---|---|---|---|---|---|
| 0 | 1 | 0.89 ± 0.04 | 2.07 ± 0.05 | 30 ± 1.5 | 7.55E3 | |
| | 2 | 1.55 ± 0.07 | 2.01 ± 0.04 | 44 ± 2 | 9.60E3 | |
| | 4 | 1.95 ± 0.09 | 1.46 ± 0.06 | 57 ± 2 | 7.75E3 | |
| | 7 | 2.12 ± 0.07 | 0.74 ± 0.08 | 74 ± 3 | 1.9E4 | 6.43 ± 0.15 |
| | 14 | 1.73 ± 0.06 | 0 | 100 | 5.4E5 | 7.00 ± 0.15 |
| 5 | 1 | 1.43 ± 0.06 | 2.37 ± 0.09 | 38 ± 2 | 1.2E4 | |
| | 2 | 1.29 ± 0.05 | 0.91 ± 0.09 | 59 ± 3 | 9.3E3 | |
| | 4 | 2.4 ± 0.1 | 0.25 ± 0.05 | 90 ± 2 | 4.4E4 | 6.44 ± 0.15 |
| | 11 | 1.29 ± 0.05 | 0 | 100 | 9.9E7 | 7.07 ± 0.15 |

An increase of the K-index above the threshold level of 60% was observed after 2 and 4 days of storage at 5° C. and 0° C. respectively. This signals the beginning of the spoilage processes in the fish meat and the drop of the fish quality although fish is still safe to consume. A spike in microbial count (indicating growth of bacteria to a spoilage level) was observed after 4 and 7 days of storage at 5° C. and 0° C. respectively. This spike is accompanied by a corresponding increase of fish juice pH from 6.4 to 7.0 and over. At this point fish is completely spoiled and is no longer suitable for consumption.

The same testing protocol was used for testing the freshness of chicken breast, trim pork (upper leg muscles) and beef. Results of K-index and pH analysis are shown in Table 2, which shows the results of K-value and pH measurements for chicken, pork and beef extracts depending on storage time and temperature.

Increase in pH from below 6.0 to 6.4 and above happens after 6 days of storage at 4° C. or 10° C., and after 2 days of storage at 15° C. More surprisingly, K-index of chicken meat stored at 15° C. actually decreases after 5 days of storage when pH becomes ~7.0. At this point samples are already heavily spoiled and a foul smell is readily detectable. It is suspected that enzymatic detection starts to underestimate K-index in the presence of other chemical products formed in badly spoiled chicken meat.

For pork stored at 0° C., 4° C., and 10° C., the K-index jumps over 70% after 6, 5, and 4 days, respectively. In the last two scenarios, the K-index falls dramatically after 6 days of storage when pH of pork juice reaches about 7.0. On the other hand, the pH of pork juice stored at 15° C. reaches about 6.5 after 2 days of storage. Thus, relatively low values of K-index for this sample could be misleading.

Finally, for beef, the K-value of 100% was measured for all tested samples regardless of temperature and time of storage (with the only exception of samples spoiled with

TABLE 2

| | | 0° C. | | 4° C. | | 10° C. | | 15° C. | |
|---|---|---|---|---|---|---|---|---|---|
| Meat | Time, days | K-value, % | pH | K-value, % | pH | K-value, % | pH | K-value, % | pH |
| Chicken | 1 | 52 ± 5 | 5.6 | 55 ± 5 | 5.7 | | 5.9 | 77 ± 5 | 6.4 |
| | 2 | 55 ± 7 | 5.9 | 56 ± 5 | 5.8 | 54 ± 5 | 6.0 | 84 ± 5 | 6.35 |
| | 3 | 42 ± 7 | 5.9 | 50 ± 7 | 6.0 | 79 ± 5 | 6.1 | 92 ± 5 | 6.5 |
| | 5 | 48 ± 5 | 5.9 | 71 ± 5 | 5.9 | 82 ± 5 | 6.3 | 100 ± 7 | 6.45 |
| | 6 | 81 ± 5 | 5.9 | 86 ± 5 | 6.4 | 98 ± 5 | 6.5 | 77 ± 5 | 6.9 |
| | 7 | 94 ± 5 | 6.0 | 98 ± 5 | 6.6 | 99 ± 5 | 6.6 | 94 ± 5 | 6.95 |
| | 14 | | 6.2 | | 6.8 | | | | |
| Pork | 1 | | 5.6 | | 5.5 | | 5.9 | | 5.8 |
| | 2 | 45 ± 7 | 5.7 | 56 ± 5 | 5.8 | 71 ± 5 | 5.9 | 47 ± 3 | 6.6 |
| | 3 | | 5.8 | | 6.0 | 68 ± 5 | 6.0 | 64 ± 5 | 6.8 |
| | 4 | | 5.8 | 62 ± 5 | 6.1 | 67 ± 5 | 6.2 | 63 ± 5 | 7.5 |
| | 5 | 59 ± 7 | 5.8 | 55 ± 5 | 6.0 | 84 ± 5 | 6.6 | 93 ± 5 | 7.6 |
| | 6 | 59 ± 7 | 5.8 | 99 ± 5 | 6.1 | 97 ± 5 | 6.9 | 65 ± 5 | 7.8 |
| | 7 | 88 ± 7 | 5.8 | 48 ± 5 | 7.0 | 58 ± 5 | 7.2 | 78 ± 5 | 7.9 |
| | 14 | | 6.2 | | 7.5 | | | | |
| Beef | 1 | 94 ± 5 | 5.5 | 99 ± 7 | 5.9 | 99 ± 7 | 6.0 | 98 ± 5 | 5.3 |
| | 2 | 100 ± 7 | 5.8 | 82 ± 10 | 5.9 | 99 ± 5 | 6.1 | 103 ± 7 | 6.5 |
| | 3 | 89 ± 7 | 5.9 | | 6.0 | 102 ± 5 | 6.3 | 85 ± 7 | 6.6 |
| | 4 | 95 ± 5 | 5.9 | | 6.1 | 93 ± 5 | 6.4 | 78 ± 5 | 6.9 |
| | 5 | 93 ± 5 | 6.0 | 105 ± 7 | 6.2 | 94 ± 7 | 6.8 | 62 ± 7 | 7.3 |
| | 6 | 83 ± 7 | 6.0 | 89 ± 7 | 6.3 | 103 ± 7 | 7.2 | 84 ± 5 | 7.5 |
| | 7 | 85 ± 7 | 6.0 | 93 ± 7 | 6.6 | 75 ± 5 | 7.5 | 68 ± 7 | 8.0 |
| | 14 | 78 ± 5 | 6.2 | 79 ± 7 | 7.0 | | | | |

The K-index of chicken breast crosses the spoilage level after 5 days of storage at 0° C., after 3 days at 4° C., after 2 days at 10° C., and after 1 day at 15° C.

bacteria as was discussed above). pH increase above 6.6 starts after 6, 4, and 2 days of storage at 5, 10, and 15° C., correspondingly.

The above data demonstrate the importance of simultaneous detection of both pH and K-index for adequate evaluation of meat/poultry/fish freshness. Although pH starts to increase only for heavy spoiled samples, it helps to correct K-index measurements that become misleading in particular conditions.

Example 2

Evaluation of Freshness of Meat/Fish by a Film with Encapsulated Sensing Element I Sensing films comprising arrays of wells in the form of patterns I and II (as described herein) were loaded with Sensing element I by both approaches and sealed onto a glass substrate.

The phosphate buffer solutions of pH ranging from pH 5.0 to 8.7 were introduced to the films and signals from sensing element were analyzed by VIS Imaging Spectrograph System for Inverted Fluorescent Microscope. Between each measurement, the film was washed two times with DI water in order to remove previous buffer. FIG. 8 shows the ratios of emission intensities $I_{585}/I_{630}$ depending on the pH for the film of Pattern I. If compared to solution emission spectra, it appears to be less dependent on pH but data fall in a single calibration curve which remains linear in the pH range from 6.5 to 8.0. Thus the films with encapsulated sensing element can be applied for meat/fish freshness assessment.

Finally the film of pattern II has been applied for assessment of freshness of the red mid-sized snakehead fish stored over 7 days at 5° C. and chicken breast stored over 7 days at 15° C. Table 3 shows data on pH of juice. It can be seen that in the case of chicken, an increase in pH was observed after day 5 indicating significant bacterial spoilage of food (compare with Table 2). The pH of fish samples remained stable over the week.

TABLE 3

| Time of storage, days | Chicken breast, 15° C. | Snakehead fish, 5° C. |
| --- | --- | --- |
| 2 | 5.87 | 6.01 |
| 3 | 6.09 | 5.99 |
| 4 | 6.04 | 6.14 |
| 5 | 6.24 | — |
| 6 | 7.09 | — |
| 7 | 6.89 | 5.98 |

APPLICATIONS

The invention can be applied as an integral part of an intelligent packaging material that can signal the freshness/quality of that particular piece of meat, poultry or seafood it has been wrapped around.

The disclosed sensor is further contemplated for other scientific and commercial applications extending beyond the food industry. The disclosed sensing films or "optical tongues" for the remote and rapid analysis of multiple analytes in aqueous solutions, could find applications in medicine, biology, healthcare and environmental monitoring. In some embodiments, the disclosed sensor may be fitted with or coupled to an optical scanner, the optical scanner being configured to detect an optical output from the sensor.

The saleable item resulting from the present disclosure is a sensing film that can be optionally attached with or retrofitted onto a typical packaging material with minimal changes required for the existing packaging technologies.

Such sensors for a single pack should have 1-2 cm in diameter and weigh less than 1 mg, on which polymer matrix is >95% wt %. The amount of dye per sensor may be in a range of a few μg. For most organic dyes, such quantities are far below established toxicity levels. Such sensors may be incorporated in every meat/poultry/seafood pack produced. The optical signal can be captured with simple and inexpensive optoelectronic measuring devices (LEDs, photodiodes, etc.) and should have minimal interference with scattering.

It will be apparent that various other modifications and adaptations of the disclosed invention will be apparent to the person skilled in the art after reading the foregoing disclosure without departing from the spirit and scope of the invention and it is intended that all such modifications and adaptations come within the scope of the appended claims.

The invention claimed is:

1. A sensor comprising a semi-permeable film layer, said semi-permeable film layer comprising at least one integrally formed well having at least one sensing element disposed therein; wherein the well is sealed by a second film layer, said semi-permeable film layer being impermeable to said sensing element but is permeable to at least one analyte detectable by said sensing element, wherein said semi-permeable film layer comprises at least two or more polyelectrolyte layers, and wherein oppositely charged polyelectrolyte layers are deposited alternately on each other.

2. The sensor of claim 1, wherein the semi-permeable layer comprises an array of integrally formed wells, wherein at least one sensing element or a mixture of sensing elements is encapsulated in each well.

3. The sensor of claim 2, wherein said mixture of sensing elements comprises two or more distinct sensing elements adapted to detect the same or different analytes.

4. The sensor of claim 1, wherein at least one well contains at least two-distinct sensing elements, each distinct sensing element adapted to detect the presence of at least one or more analytes.

5. The sensor of claim 1, wherein the molecular weight cut-off (MWCO) of the semi-permeable layer is from about 1 to 20 kDa.

6. The sensor of claim 1, wherein the analytes are chemical or biochemical markers produced during muscle cell autolysis or bacterial growth.

7. The sensor of claim 1, wherein the analytes are selected from the group consisting of: $H^+$ ions, hypoxanthine, inosine, inosine monophosphate, n-butyrate, L-lactic acid, D-lactate, acetic acid, ethanol, and biogenic amines.

8. The sensor of claim 7, wherein the analytes are selected from the group consisting of: hypoxanthine, inosine and inosine monophosphate.

9. The sensor of claim 1, wherein said sensing elements provide at least one measurable property upon detecting said analytes.

10. The sensor of claim 9, wherein the measurable property is fluorescence.

11. The sensor of claim 1, wherein at least one well contains a sensing element capable of detecting a change in pH and at least one well contains a sensing element capable of detecting hydrogen peroxide.

12. The sensor of claim 1, wherein the sensing elements are selected from the group consisting of: fluorescent dyes and enzymes.

13. The sensor of claim 1, wherein said second film layer is optically translucent or transparent.

14. This sensor of claim 13, wherein said second film layer is a semi-permeable layer.

15. This sensor of claim 14, wherein said second film layer is not permeable to said sensing element but is permeable to said analytes.

16. The sensor of claim 1, wherein said second film layer comprises at least one exposed surface not engaged with said semi-permeable film layer, said exposed surface being an adhesive surface or comprising means for adhesion to a substrate surface.

17. The sensor of claim 16, wherein said exposed surface comprises an adhesive layer.

18. A method of assessing food quality in packaged food, the method comprising the steps of: a) contacting a sensor according to claim 1 with said food; b) detecting at least one measurable output from said sensor.

19. A method of making a sensor, said method comprising the steps of:
- depositing a semi-permeable film coating on a patterned template to thereby form a semi-permeable film layer having at least one integrally formed well;
- disposing one or more sensing elements in said well; and encapsulating said sensing elements in said well;
- wherein said semi-permeable film layer is not permeable to said sensing element but is permeable to at least one analyte detectable by said sensing element, wherein said semi-permeable film layer comprises at least two or more polyelectrolyte layers, and wherein oppositely charged polyelectrolyte layers are deposited alternately on each other.

* * * * *